(12) United States Patent
Iimori

(10) Patent No.: US 7,565,274 B2
(45) Date of Patent: Jul. 21, 2009

(54) METHOD AND APPARATUS FOR PREDICTING BENDING LIFE SPANS OF ELECTRIC WIRES AND OR WIRE PROTECTING MEMBERS INDUCED BY VIBRATIONS, AND RECORDING MEDIUM STORING PROGRAM

(75) Inventor: Yasuo Iimori, Kosai (JP)

(73) Assignee: Yazaki Corporation, Tokyo (JP)

( * ) Notice: Subject to any disclaimer, the term of this patent is extended or adjusted under 35 U.S.C. 154(b) by 766 days.

(21) Appl. No.: 10/534,069

(22) PCT Filed: Nov. 25, 2003

(86) PCT No.: PCT/JP03/15015

§ 371 (c)(1),
(2), (4) Date: May 6, 2005

(87) PCT Pub. No.: WO2004/048940

PCT Pub. Date: Jun. 10, 2004

(65) Prior Publication Data
US 2006/0052990 A1   Mar. 9, 2006

(30) Foreign Application Priority Data

Nov. 28, 2002 (JP) .............................. 2002-345220
Oct. 24, 2003 (JP) .............................. 2003-364516

(51) Int. Cl.
*G06F 17/10* (2006.01)
(52) U.S. Cl. .................. 703/2; 703/7; 702/42; 73/812
(58) Field of Classification Search .................. 703/1, 703/2, 6, 7; 702/42; 73/812
See application file for complete search history.

(56) References Cited

U.S. PATENT DOCUMENTS 6,439,059 B1 * 8/2002 Inoue et al. .................... 73/812
6,839,642 B2 * 1/2005 Kawakita et al. .............. 702/42
6,961,683 B2 * 11/2005 Kodama et al. ................ 703/2

FOREIGN PATENT DOCUMENTS

EP   1 236 989 A2   9/2002

OTHER PUBLICATIONS

Fox et al., A. The Effect of Gold-Tin Intermetallic Compound on the Low Cycle Fatigue Behavior of Copper Alloy C72700 and C17200 Wires, IEEE Transactions on Components, Hybrids, and Manufacturing Technology, vol. CHMT-9, No. 3, Sep. 1986, pp. 272-278.*

(Continued)

*Primary Examiner*—Russell Frejd
(74) *Attorney, Agent, or Firm*—Sughrue Mion, PLLC

(57) ABSTRACT

In a method for predicting bending life spans of wires, the wires, temperatures, pre-vibration shapes, and constraint conditions are set, and finite element models of the electric wires are formed using a finite element method. Natural frequencies for the pre-vibration shapes are calculated, and stresses in individual finite elements of the finite element models which correspond to the natural frequencies are calculated, and a maximum stress is retrieved. Predicting functions corresponding to the plural electric wires and the atmosphere temperatures, which are set, are read out. A bending life span corresponding to the maximum stress of each electric wire, is acquired while referring to the predicting functions read out, and a shortest bending life span is obtained from the bending life spans, and output.

15 Claims, 7 Drawing Sheets

OTHER PUBLICATIONS

Miyazaki et al., S. Fatigue life of Ti-50 at.% Ni and Ti-40Ni-10Cu (at.%) shape memory alloy wires, Materials, Science and Engineering, vol. 273-275, Dec. 1999, pp. 658-663.*

Zhou et al., Z.R. Single wire fretting fatigue tests for electrical conductor bending fatigue evaluation, Wear, vol. 181-183, Mar. 1995, pp. 537-543.*

Chiang, Y.J. Characterizing simple-stranded wire cables under axial loading, Finte Elements in Analysis and Design, vol. 24, Dec. 1996, pp. 49-66.*

Flowers G T, et al, Vibration Thresholds for Fretting Corrosion in Electrical Connectors, Electrical Contacts-2002. Proceedings of the 48$^{TH}$., IEEE HOLM Conference on Electrical Contacts., Orlando, FL, Oct. 21-23, 2002, IEEE HOLM Conference on Electrical Contacts Sponsors, New York, NY IEEE, US vol. Conf. 48, Oct. 21, 2002, pp. 133-139.

Schmidt P A et al:, "Development of a Novel Specimen Geometry for Fatigue Testing of Fine Wire" Journal of Testing and Evaluation, American Society for Testing and Material, Philadelphia, US, vol. 23, No. 2, Mar. 1, 1995, pp. 73-79.

International Search Report dated Nov. 26, 2004.

B. Nasu, "Matrix Infinite Element Method" (1978) Brain Library Publishing Corp., pp. 7 to 15.

Kimihiko Yasuda, "Mode Analysis and Dynamic Design" (1993) Corona Corp., pp. 54 to 56.

* cited by examiner

METHOD AND APPARATUS FOR PREDICTING BENDING LIFE SPANS OF ELECTRIC WIRES AND OR WIRE PROTECTING MEMBERS INDUCED BY VIBRATIONS, AND RECORDING MEDIUM STORING PROGRAM

TECHNICAL FIELD

The present invention relates to a method and apparatus for predicting bending life spans of a plurality of electric wires clamped at least at two points to a predetermined part and/or their wire protecting members, the bending induced by vibrations, and a program for predicting the same.

BACKGROUND ART

Usually, in a vehicle or the like, a plurality of electric devices are electrically connected to one another by a plurality of electric wires (referred to frequently and simply as wires). The wires are bundled, by an insulation locking band, tape or the like, into a single bundle as so-called wire harness which is extendedly arranged at predetermined locations of the automobile or the like. In some eases, the wires are protected by a wire protecting member such as a grommet, and are arranged at a predetermined part. In other cases, the wires are arranged at a predetermined part of the vehicle or the like, while not bundled into one line and/or not protected by the wire protecting members.

The vehicle is always placed in such an environment that it is always vibrated due to engine drive and the like. In particular, the electric wires distributed inside the engine room directly receiving the engine vibrations, are repeatedly bent and deformed, and finally disconnect due to the vibrations. Experimental results of such are reported. In this respect, it is of particular importance to accurately predict the bending life spans of the electric wires and the wire protecting members.

Generally, the prediction of the bending life spans of the electric wires and the wire protecting members is carried out by repeating design, trial manufacturing, and endurance test. For example, in such an endurance test, wires distributed along an envisioned wiring path are placed on a vibration base plate. The vibration base plate is vibrated at a predetermined frequency and a predetermined amplitude by the vibrator, and a bending life span of the wire when it is vibrated at a specific number of vibrations is predicted.

The literature cited in the present specification are: Non-patent document 1
"Matrix Infinite Element Method" by B. Nasu, published by Brain Library Publishing Corp, Aug. 10, 1978, pp 7 to 15
Non-patent document 2
"Mode Analysis and Dynamic Design" by Kimihiko Yasuda, published by Corona Corp, Nov. 10, 1993, pp 54 to 56

On the other hand, a development period of the vehicle tends to be shorter, and further there is a demand of enhancing a bending life prediction accuracy. In this circumstance, the related bending life span predicting method in which the endurance test is repeated cannot satisfactorily reduce the development period, and cannot sufficiently meet the demand of enhancing the prediction accuracy.

DISCLOSURE OF THE INVENTION

Accordingly, to cope with the above-mentioned problems, an object of the present invention is to provide a method and apparatus for predicting bending life spans of electric wires, which can meet the demands of a highly accurate prediction of the bending life span and of reducing the development period in an environment where vibrations occur, and a recording medium storing a program for predicting the same in such ways.

In order to solve the aforesaid object, the invention is characterized by having the following arrangement.

(1) A bending life predicting method of predicting bending life span of a plurality of wires induced by vibration, at least two points of each of the plurality of wires being constrained, the method comprising the steps of:

a pre-storing step of pre-storing each predicting function representing relationships among atmosphere temperatures, stresses and bending life spans for the plurality of wires;

a setting step of setting the plurality of wires, the atmosphere temperatures, pre-vibration shapes of the plurality of wires, and constraint conditions of the plurality of wires;

a finite element model forming step of forming finite element models of the plurality of wires by using a finite element method;

a vibration analyzing step of calculating natural frequencies for the pre-vibration shapes and calculating stresses in individual finite elements of the finite element models which correspond to the natural frequencies, respectively;

a maximum stress retrieving step of retrieving a maximum stress from the stresses calculated in the vibration analyzing step, for each of the plurality of wires;

a predicting function readout step of reading predicting functions corresponding to the atmosphere temperatures set in the setting step, respectively;

a bending life predicting step of acquiring a bending life span corresponding to the maximum stress of each of the plurality of wires while referring to the predicting functions read out in the predicting function readout step, and obtaining a shortest bending life span from the bending life spans; and an output step of outputting the shortest bending life span obtained in the bending life predicting step.

(2) The method according to (1), wherein in the vibration analyzing step, the plurality of wires are regarded as a wiring structure in which the plurality of wires are bundled, and natural frequencies of the plurality of wires are computed, respectively.

(3) The method according to (1), wherein the plurality of wires are bundled into a single bundle, and the bundling of the plurality of wires is set as one of the constraint conditions in the setting step.

(4) The method according to (1), further comprising a position specifying step of specifying a position on the wire corresponding to the shortest bending life span, the output step outputting the position specified by the position specifying step.

(5) The method according to (1), wherein
in the vibration analyzing step, displacements of finite elements of the finite element models which correspond to the natural frequencies are calculated,
the method includes an interference part predicting step of predicting an interference part on the plurality of wires which is induced by vibrations based on the calculated displacements, and
the output step outputs the predicted interference part.

(6) The method according to (1), wherein a curve representing a lower confidence interval to a population regression function statistically calculated using the stresses and data on bending endurance life spans that are obtained under a plurality of typical atmosphere temperatures for the plurality of wires, is used for the predicting function.

(7) A bending life predicting method of predicting bending life spans of a plurality of electric wires and wire protecting members for protecting the plurality of wires from being bent induced by vibrations, at least two points of each of the plurality of wires being constrained, the method comprising:

a pre-storing step of pre-storing relationships among atmosphere temperatures, stresses and bending life spans for plurality of wires and the wire protecting member;

a setting step of setting the plurality of wires, the wire protecting member, the atmosphere temperatures, pre-vibration shapes of the plurality of wires and the wire protecting member, and constraint conditions of the plurality of wires and the wire protecting member;

a finite element model forming step of forming finite element models of the plurality of wires and the wire protecting member by using a finite element method;

a vibration analyzing step of calculating natural frequencies for the pre-vibration shapes of the plurality of wire and the wire protecting member, and calculating stresses in individual finite elements of the finite element models which correspond to the natural frequencies, respectively;

a maximum stress retrieving step of retrieving maximum stresses from the stresses calculated in the vibration analyzing step, for each of the plurality of wires and the wire protecting member;

a predicting function readout step of reading predicting functions corresponding to atmosphere temperatures set in the setting step;

a bending life predicting step of acquiring bending life spans corresponding to the maximum stresses of the plurality of wires and the wire protecting member, while referring to the predicting functions read out in the predicting function readout step, respectively, and obtaining a shortest bending life span from said bending life spans; and an output step of outputting the shortest bending life span obtained in the bending life predicting step.

(8) The method according to (7), wherein in the vibration analyzing step, the plurality of wires are regarded as a wiring structure in which the plurality of wires are bundled, and natural frequencies of the plurality of wires are computed, respectively.

(9) The method according to (7), wherein the plurality of wires are bundled into a single bundle, and the bundling of the plurality of wires is set as one of the constraint conditions in the setting step.

(10) The method according to (7), further comprising a position specifying step of specifying a position on the wire or the wire protecting member corresponding to the shortest bending life span, the output step outputting the position specified by the position specifying step.

(11) The method according to (7), wherein in the vibration analyzing step, displacements of finite elements of the finite element models which correspond to the natural frequencies are calculated, the method includes an interference part predicting step of predicting an interference part on the plurality of wires which or the wire protecting member is induced by vibrations based on the calculated displacements, and the output step outputs the predicted interference part.

(12) The method according to (7), wherein a curve representing a lower confidence interval to a population regression function statistically calculated using the stresses and data on bending endurance life spans that are obtained under a plurality of typical atmosphere temperatures for the plurality of wires and the wire protecting member, is used for the predicting function.

(13) A bending life predicting device for predicting bending life spans of a plurality of wires induced by vibrations, at least two points of each of the plurality of wires being constrained, the device comprising:

a pre-storing unit for pre-storing each predicting function representing relationships among atmosphere temperatures, stresses and bending life spans for the plurality of wires;

a setting unit for setting the plurality for wires, the atmosphere temperatures, pre-vibration shapes of the plurality of wires, and constraint conditions of the plurality of wires;

a finite element model forming unit for forming finite element models of the plurality of wires by using a finite element method;

a vibration analyzing unit for calculating natural frequencies for the pre-vibration shapes and calculating stresses in individual finite elements of the finite element models which correspond to the natural frequencies, respectively;

a maximum stress retrieving unit for retrieving a maximum stress from the stresses calculated in the vibration analyzing unit, for each of the plurality of wires;

a predicting function readout unit for reading predicting functions corresponding to the atmosphere temperatures set in the setting unit, respectively;

a bending life predicting unit for acquiring a bending life span corresponding to the maximum stress of each of the plurality of wires while referring to the predicting functions read out in the predicting function readout unit, and obtaining a shortest bending life span from the bending life spans; and an output unit for outputting the shortest bending life span obtained in the bending life predicting unit.

(14) The device according to (13), wherein the vibration analyzing unit calculates displacements of finite elements of the finite element models which correspond to the natural frequencies, the device includes an interference part predicting unit for predicting an interference part on the plurality of wires which or the wire protecting member is induced by vibrations based on the calculated displacements, and the output unit outputs the predicted interference part.

(15) A computer readable recording medium storing a program for predicting bending life spans of a plurality of wires induced by vibrations, at least two points of each of the plurality of wires being constrained, the program causing a computer to function as:

a pre-storing unit for pre-storing each predicting function representing relationships among atmosphere temperatures, stresses and bending life spans for the plurality of wires;

a setting unit for setting the plurality for wires, the atmosphere temperatures, pre-vibration shapes of the plurality of wires, and constraint conditions of the plurality of wires;

a finite element model forming unit for forming finite element models of the plurality of wires by using a finite element method;

a vibration analyzing unit for calculating natural frequencies for the pre-vibration shapes and calculating stresses in individual finite elements of the finite element models which correspond to the natural frequencies, respectively;

a maximum stress retrieving unit for retrieving a maximum stress from the stresses calculated in the vibration analyzing unit, for each of the plurality of wires;

a predicting function readout unit for reading predicting functions corresponding to the atmosphere temperatures set in the setting unit, respectively;

a bending life predicting unit for acquiring a bending life span corresponding to the maximum stress of each of the plurality of wires while referring to the predicting functions read out in the predicting function readout unit, and obtaining a shortest bending life span from the bending life spans; and an output unit for outputting the shortest bending life span obtained in the bending life predicting unit.

BEST MODE FOR CARRYING OUT THE INVENTION

Figure 2A:
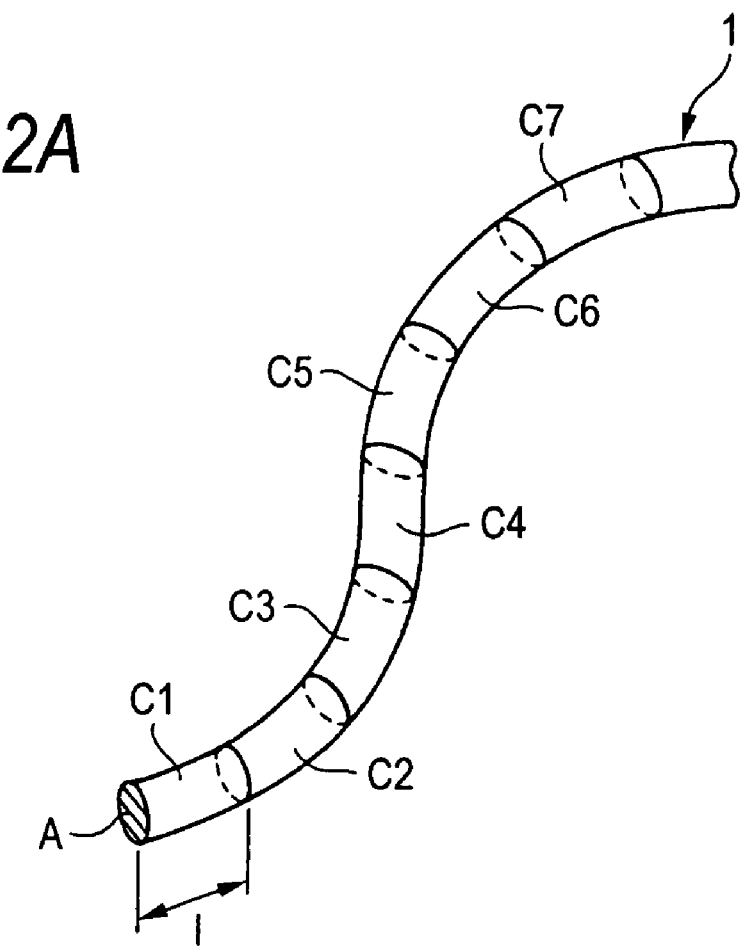
FIG. 2A is a diagram showing an electric wire handled in the invention when it is discretized.
Figure 2B:
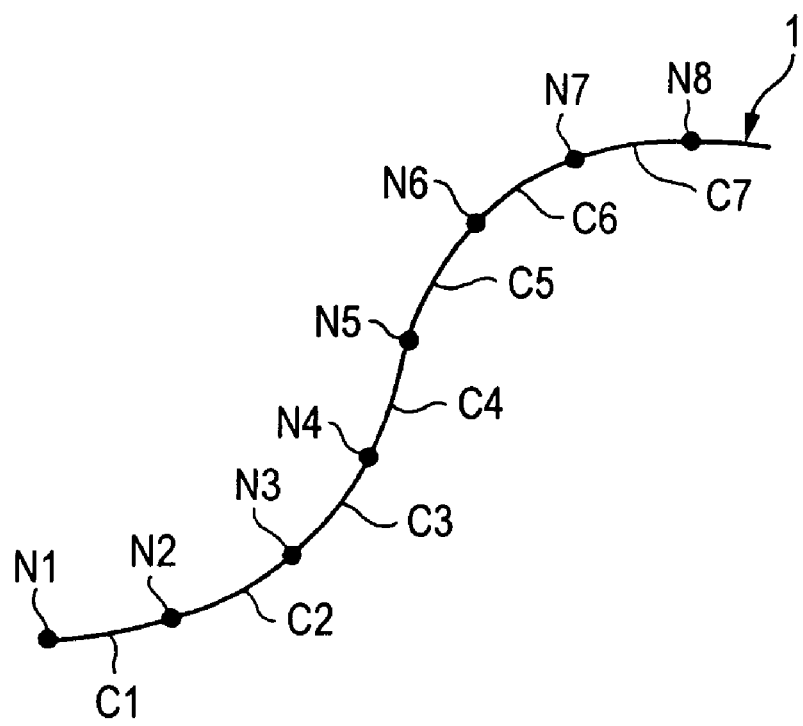
FIG. 2B is a diagram showing beam elements and nodes of the discrete electric wire shown in FIG. 2A.

The preferred embodiment according to the present invention will be described with reference to the accompanying drawings. Pre-conditions, theories and basic formulae which are used in the embodiment will first be described with reference to FIGS. 2A and 2B. FIG. 2A is a diagram showing an electric wire in a state it is discretized, handled in the invention. FIG. 2B is a diagram showing beam elements and nodes of the discrete electric wire shown in FIG. 2A.

In the invention, a finite element method is utilized on the basis of the following assumptions:
(1) The electric wire consists of an elastic member.
(2) The electric wire is an aggregation of beam elements serially connected to one another.
(3) A linearity is retained in each beam element.
(4) A cross section of the electric wire is circular.

Next, this electric wire 1 is discretized. Specifically, as shown in FIG. 2A, the electric wire 1 is divided (discretized) into plural beam elements C1, C2, C3, . . . . In other words, the electric wire 1 is regarded as an aggregation of a finite number of beam elements serially connected to one another.

Accordingly, the electric wire 1 may be considered as an aggregation of beam elements C1, C2, C3, . . . which are serially connected at nodes N1, N2, N3, . . . to one another, as shown in FIG. 2B. Properties necessary for the beam element are, for example, length "l" (see FIG. 2A), a cross section area A (see FIG. 2A), a moment of inertia of area, a polar moment of inertia of area, density, a modulus of longitudinal elasticity, a modulus of transverse elasticity, and the like. Those properties may be obtained in advance by measurement or calculation. It is preferable that the properties are formed as a database, and available ad libitum. In the specification, the length and the cross sectional area are set as geometric properties, and the moment of inertia of area, the polar moment of inertia of area, the modulus of longitudinal elasticity, and the modulus of transverse elasticity are set as material properties.

As well known, Hook's Law holds for a displacement of a structure not being vibrating by a static force within a range of elasticity of the structure. Likewise, Hook's Law holds also for the beam elements C1, C2, C3, . . . , as is known. The conditions of the displacement continuity and the equilibrium of forces are satisfied among the adjacent beam elements C1, C2, C3, . . . . By utilizing those facts, those beam elements C1, C2, C3, . . . are connected and the resultant discrete body (electric wire) is expressed by the following expression (1).

$$[K]\{x\}=\{F\} \tag{1}$$

In the above expression, [K] is a global stiffness matrix which are assembled from stiffness matrices of individual beam elements. To state it simply, the contents of the global stiffness matrix [K] is like an aggregation of the properties. Those values are previously set. $\{x\}$ is a nodal displacement vector (or a displacement vector, simply), and an array of displacement components of all the nodes. The component of the nodal displacement vector $\{x\}$ includes a preset vector, such as a point of constraint, and an unknown quantity. $\{F\}$ is a net external force vector, and an array of external force components at all the nodes.

In this way, a finite element model of the discrete wire having divided into an optional number of beam elements is formed. A technique, which is similar to a technique disclosed in Japanese patent application No, 2002-279503, filed on Sep. 25, 2002 by the Applicant of the present patent application, can be applied to the formation of the finite element model. The general matrix finite element method is described in, for example, the non-patent documents described above.

In the invention, to predict a bending life span of the electric wire induced by vibrations, it is necessary to obtain the natural frequencies, displacements, stress and the like. A theory and calculation formulae, which are used for obtaining the natural frequencies, displacements, stress and the like, will be briefly described below, while developing the expression (1).

To dynamically handle the wire for predicting its bending life span, an inertia force $[M]\{x''\}$ is added to the load term in the expression of the static equilibrium expressed by the expression (1), and damping $[C]\{x'\}$ is taken into account, and then we have $$[M]\{x''\}+[C]\{x'\}+[K]\{x\}=\{F(t)\} \tag{2}$$

where
[M]: inertia matrix
[C]: damping coefficient matrix
$\{x'\}$: first order differential of the displacement vector $\{x\}$
$\{x''\}$: second order differential of the displacement vector $\{x\}$ In a free vibration state, if external force=0 ($\{F(t)\}$=0 in the expression (2)), and no damping is present [C] $\{x'\}$=0 in the expression (2)), each point of the wire oscillates in a simple harmonic motion at a fixed frequency. When the following expression (3) is substituted into the expression (2), $$\{x\}=\{x_o\}\sin \omega t \tag{3}$$

then we have $$[M](\{x_o\}\sin \omega t)''+[K](\{x_o\}\sin \omega t)=0 \ (-\omega^2[M]+[K])$$
$$\{x\}\sin \omega t=0 \ ([K]-\omega^2[M])\{x\}=0 \tag{4}$$

From the expression (4), the natural frequency ω and the displacement vector $\{x\}$ as an eigen-vector can be obtained. Even if the displacement vector $\{x\}$ is multiplied by a fixed number, the expression (4) holds. Hence, the displacement vector $\{x\}$ is a relative displacement. Accordingly, a stress obtained from the displacement vector $\{x\}$ is also a relative value. An absolute value obtained from the expression (4) is only the natural frequency ω. To calculate actual displacements and stresses, it is necessary to input a load condition of an actual vibration.

To dynamically handle the wire for its bending life span prediction, if the time-dependant load {F (t)} is input to the expression (2), displacements and stresses each for each unit time can be calculated, basically. In case where the equation is solved by inputting the time-dependant load {F(t)} to the expression (2), an analysis time to reproduce the vibration is long in a phenomenon attendant with periodic vibrations, and hence, a time to output the analysis result is extremely long. To avoid this, a common practice is to convert the expression from a time domain to a frequency domain by Fourier transformation. In the calculation of the expression in the frequency domain, viz., in the frequency response analysis, the frequency-dependant load is input to the expression to calculate displacement and stress per each frequency. For the frequency-dependant load, a force applied to points of constraint on a wire harness or a wire protecting member as an object under prediction of the bending life is set at an optional value, the force attending envisioned vibrations of the engine, vehicle body, and the like. Thereafter, the expression is returned from the frequency domain to the time domain by inverse Fourier transformation, whereby an amount of calculation is reduced. This technique is well known, and hence, no further description of it will be given here.

By utilizing the theories and calculation formula thus far described, one can calculate natural frequency, displacements and stresses, which will be described later on. The general eigenvalue analysis as described above is described also in the non-patent document 2, for example.

In the present invention, a vibration analysis of a plurality of electric wires including, for example, grommets as wire protecting members is also carried out. To apply the finite element method to the wire protecting member, the wire protecting member is divided into a plurality of triangular finite elements, and stresses at those finite elements are obtained. A vibration analysis of the wire protecting member, which follows the formation of the finite element model consisting of such finite elements, is carried out in a manner as in the case of the electric wire.

Figure 3:
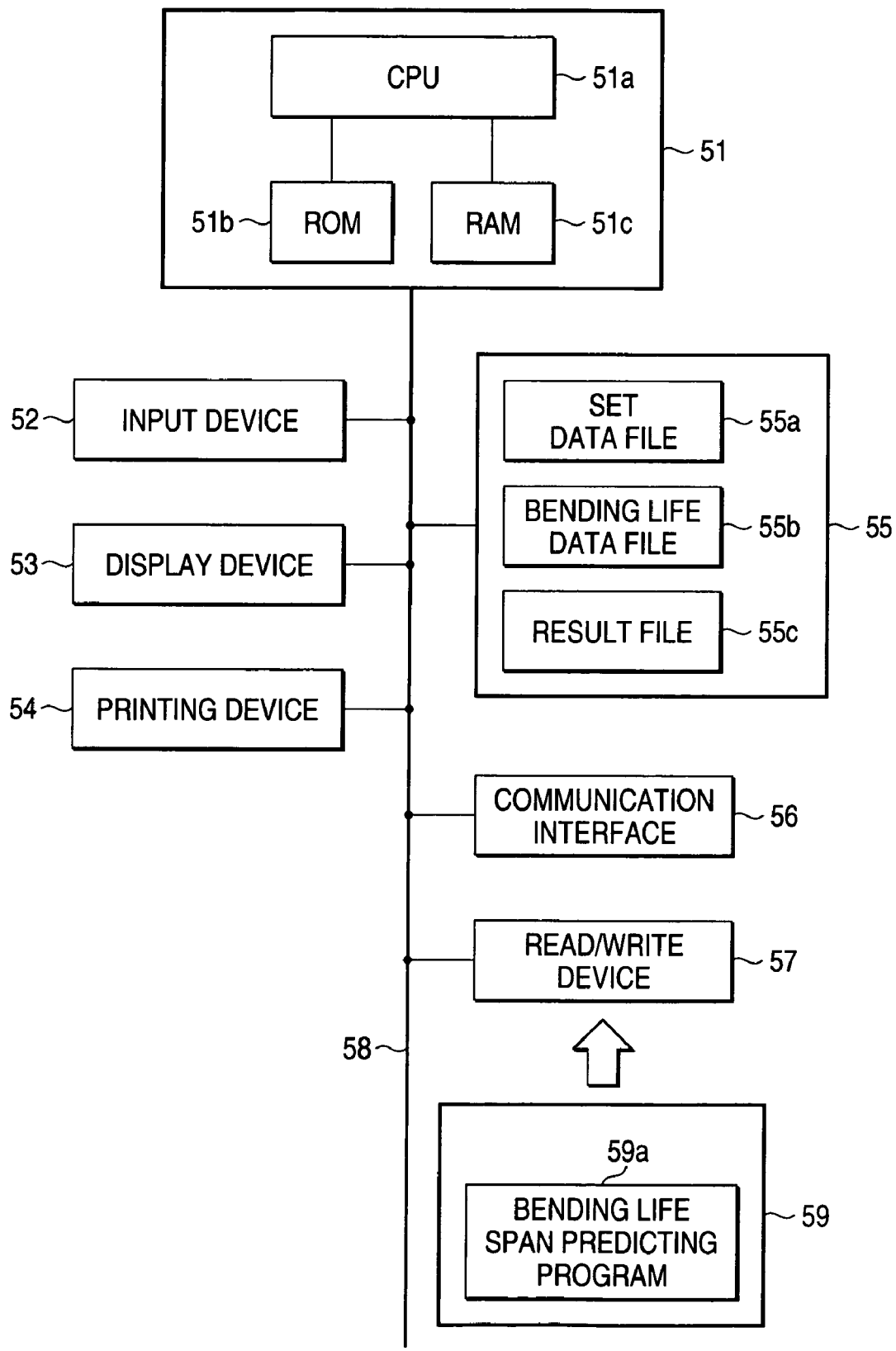
FIG. 3 is a block diagram showing a hardware configuration constructed according to the invention.
Figure 4A:
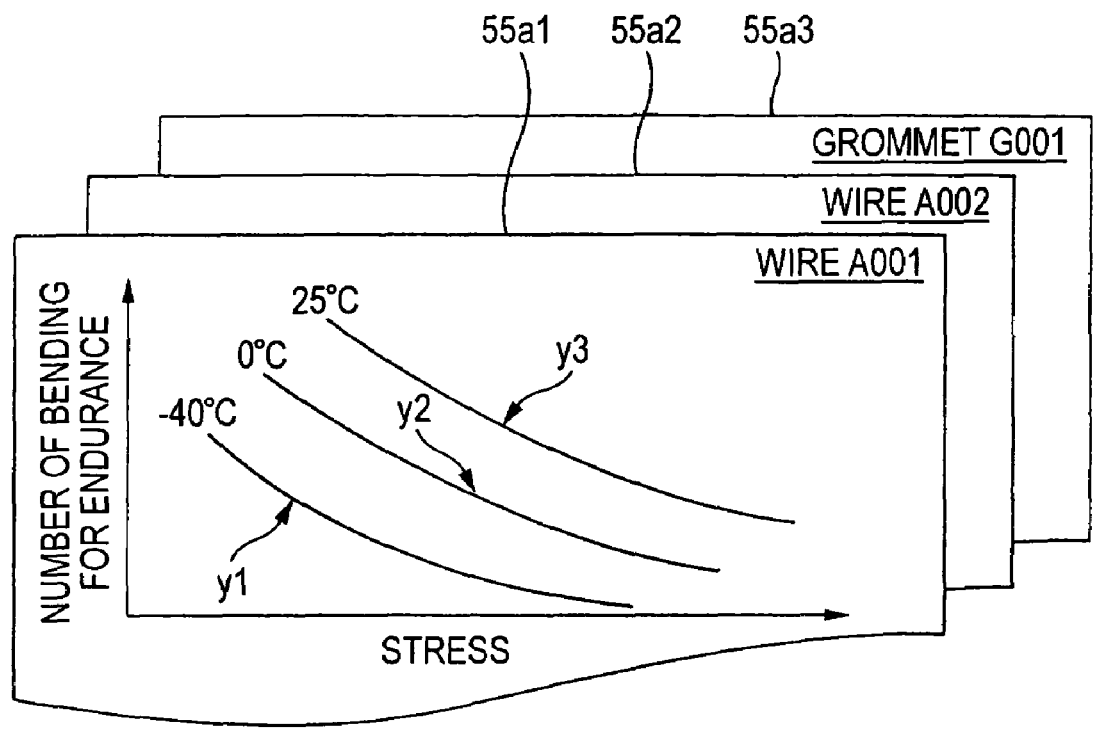
FIGS. 4A and 4B are diagrams showing bending life span data stored in a storing device in FIG. 3.
Figure 4B:
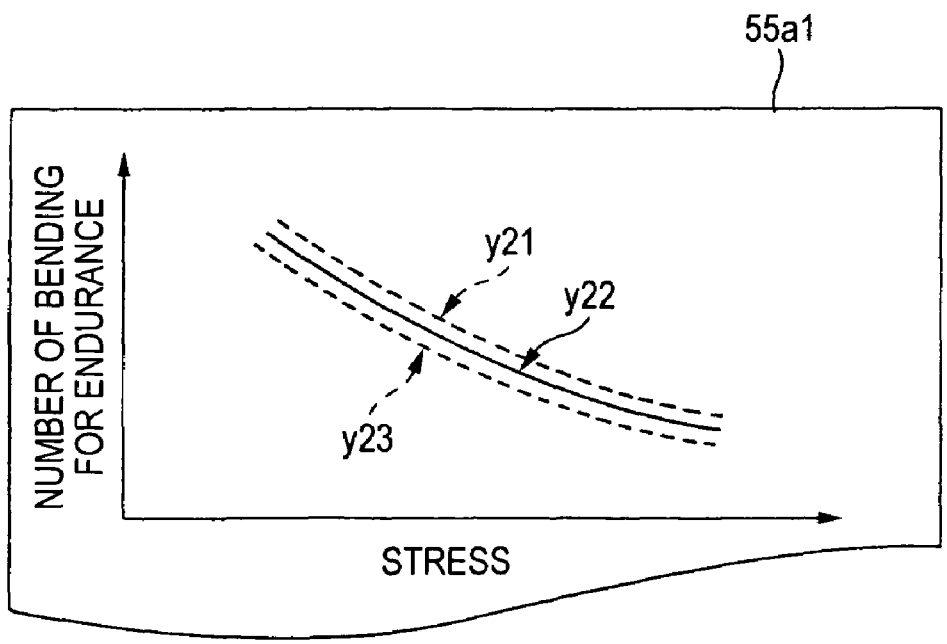

Next, a hardware configuration for realizing a process procedure constructed according to the present invention will be described. FIG. 3 is a block diagram showing a hardware configuration constructed according to the invention. FIGS. 4A and 4B are diagrams showing bending life span data stored in a storing device in FIG. 3.

As shown in FIG. 3, in the present invention, a personal computer, for example, is used which has a basic configuration made up of a micro-computer 51, an input device 52, a display device 53, a printing device 54, a storing device 55, a communication interface 56, and a read/write device 57. The micro-computer 51 includes a CPU (central processing unit) 51a, a ROM 51b for storing a boot program and others, and a RAM 51c for temporarily storing various processing results. The input device 52 is a keyboard, a computer mouse and the like; the display device 53 is an LCD, a CRT and the like for displaying processing results; and the printing device 54 is a printer for printing processing results.

The storing device 55 is, for example, a hard disc drive, and the communication interface 56 is, for example, a modem board for communicating with external devices by way of an internet, a LAN line and the like. The read/write device 57 reads a bending life span predicting program 59a constructed according to the invention, which is stored in a recording medium 59, and writes a result file 55c into the recording medium 59. Those constituent components are interconnected through an internal bus 58.

At least a set data file 55a, a bending life data file 55b, and a result file 55c are stored in the storing device 55. The set data file 55a contains data preset for predicting the bending life span. The data represents types of electric wires and wire protecting members, atmosphere temperatures, pre-vibration shapes, constraint conditions and others, which are set in a step S1 to be described later. The set data file 55a contains position information of obstacles 2, such as pre-estimated stays and electric parts (see FIG. 7).

The bending life data file 55b is an aggregation of predicting functions y1, y2 and y3 as statistically calculated using data of stresses and the number of bendings for endurance on electric wires 55a1 and 55a2, and wire protecting member (e.g., grommet) 55a3, which are gathered at different atmosphere temperatures of, for example, −40° C., 0° C. and 25° C.

A curve y22 represents an upper confidence interval and the curve y23 represents a lower confidence interval to a population regression function y21 obtained by the known regression analysis, as shown in FIG. 4B. For the predicting function, the curve y23 of those curves y22 and y23 is used. The confidence interval is, for example, 95%. Such predicting functions are obtained under condition that the electric wire and the grommet are placed at different atmosphere temperatures. Accordingly, the bending life span is predicted under more severe statistical conditions. As a matter of course, a given statistical reliability on the predicting function is taken into account, and a computing process of the predicting function is easy. As a result, the bending life span is severely predicted without addition of complicated processing procedures. This contributes to further enhancement of quality and wiring path plan. Incidentally, the number of bendings for endurance may be obtained using the population aggression function.

The result file 55c contains all the stresses of the discrete wire and the discrete grommet in the finite elements, which are recorded by each natural frequency. The result file 55c is stored in a text format, and may be output ad libitum. The storing device 55 corresponds to predicting function storing means set forth in claims.

With such a configuration, the micro-computer 51 installs a bending life span predicting program 59a that is read by the read/write device 57 into the storing device 55. After power on, the micro-computer 51 is activated according to a boot program that is stored in the ROM 51b, and starts the bending life span predicting program 59a. According to the bending life span predicting program 59a, the micro-computer 51 predicts a bending life span of the electric wire and/or the wire protecting member induced by vibrations, causes the display device 53 and the printing device 54 to display and print the prediction result, and stores the result in the storing device 55. The bending life span predicting program 59a may be installed to another personal computer having the same configuration, and after installing, operates the computer as a bending life predicting device. The bending life span predicting program 59a may be provided through a communication line, such as an Internet, a LAN or the like, instead of the recording medium 59.

Figure 5:
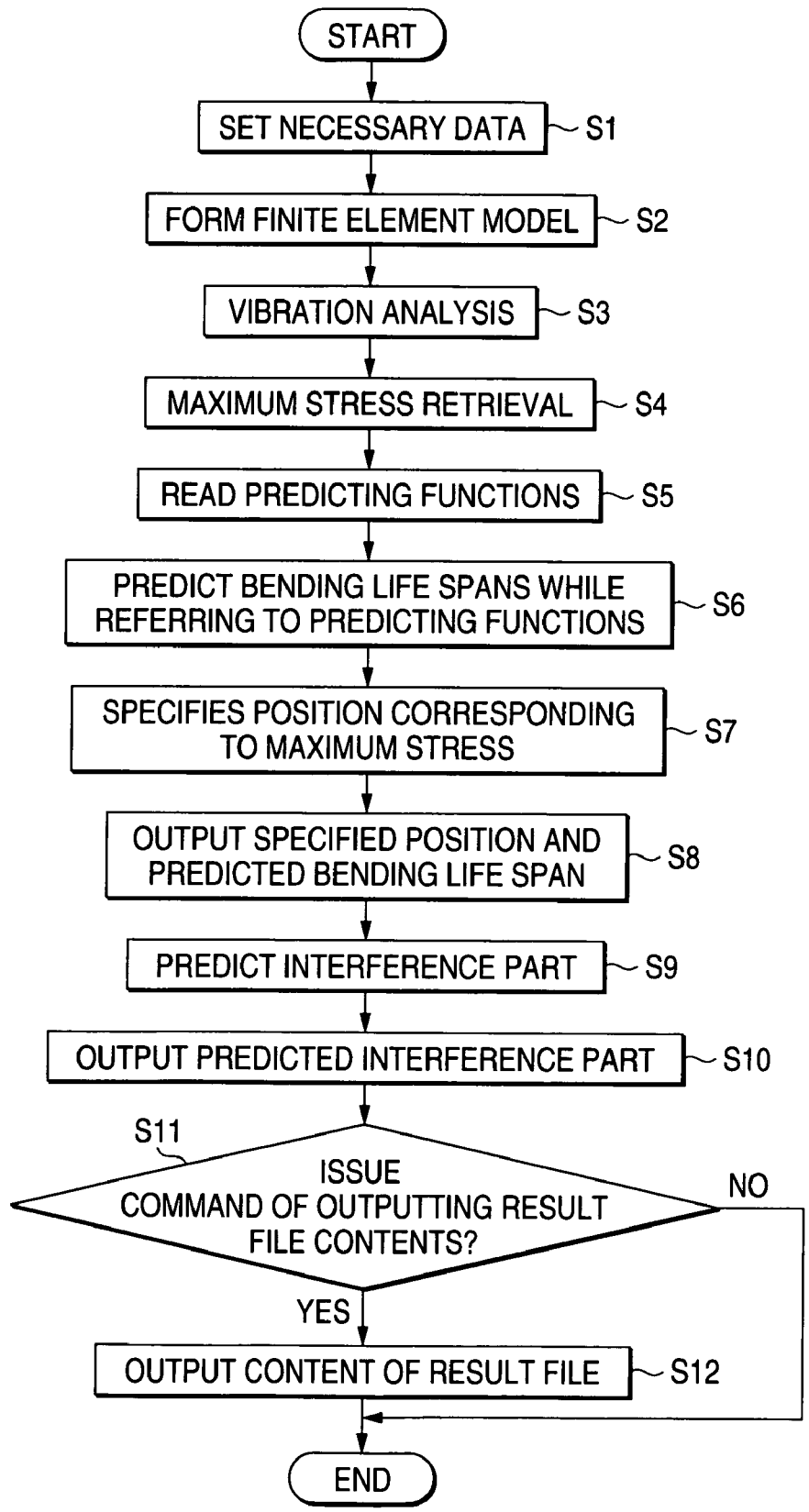
FIG. 5 is a flow chart showing a main processing procedure according to an embodiment of the invention.
Figure 6:
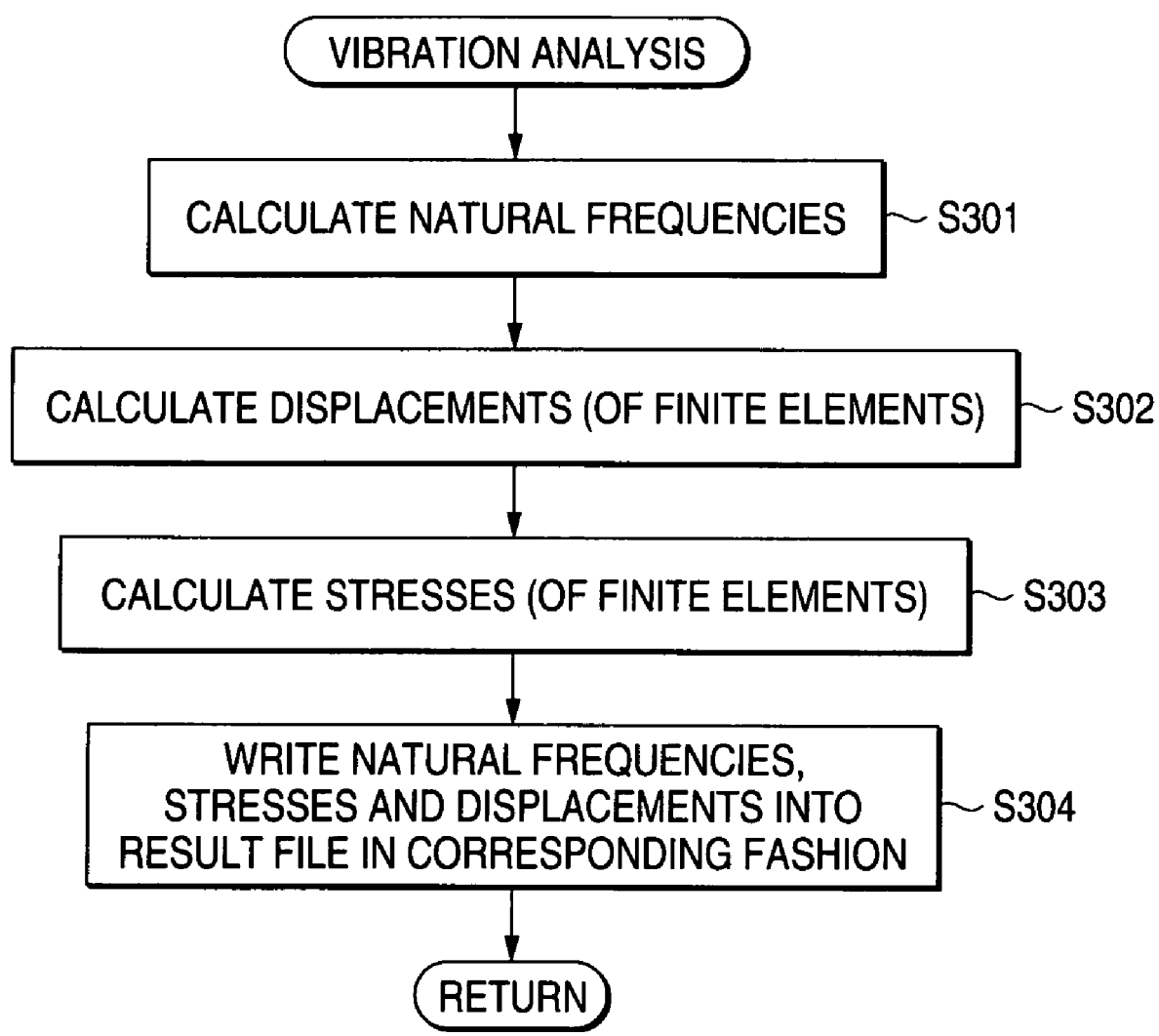
FIG. 6 is a flow chart showing a vibration analysis processing procedure shown in FIG. 5.
Figure 7A:
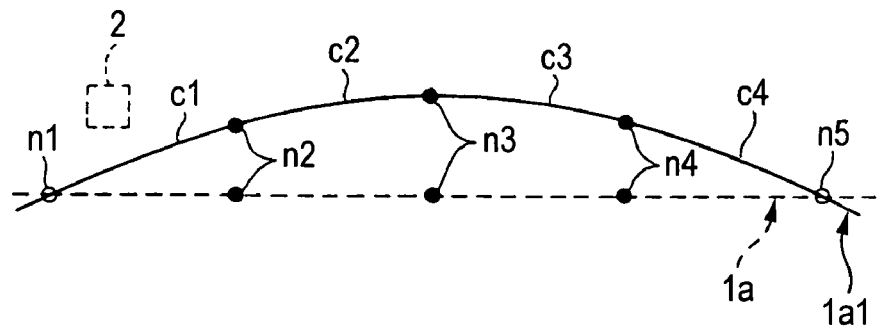
FIGS. 7A, 7B and 7C are diagrams showing predictive shapes of the electric wire in primary, secondary and tertiary vibration modes, respectively.
Figure 7B:
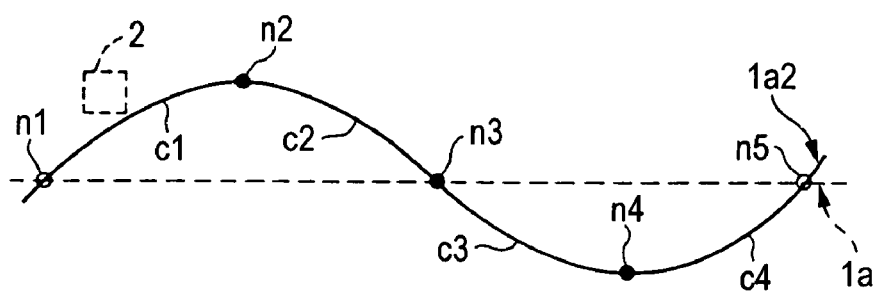
Figure 7C:
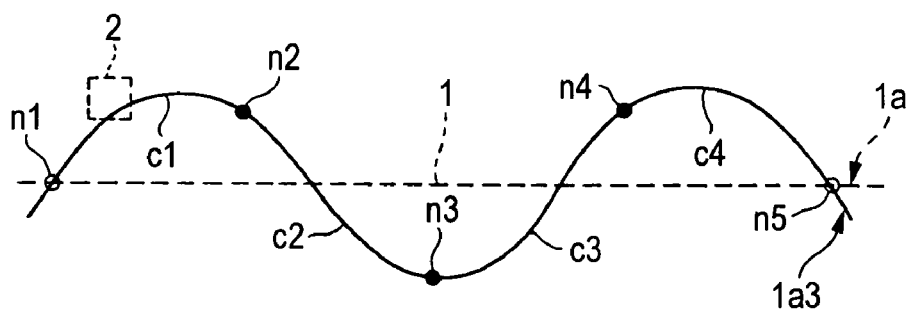

Processing procedures according to the present embodiment of the invention will be described using an explanatory diagram of FIGS. 7A through 7C and flow charts of FIGS. 5 and 6. FIG. 5 is a flow chart showing a main processing procedure according to an embodiment of the invention. FIG. 6 is a flow chart showing a vibration analysis processing procedure shown in FIG. 5. FIGS. 7A, 7B and 7C are diagrams showing predictive shapes of the electric wire in primary, secondary and tertiary vibration modes, respectively.

As shown in FIG. 5, data necessary for the prediction is set in a step S1. Specifically, items to be set are at least a plurality of electric wires (exactly types of electric wires) whose bending life spans are to be predicted, wire protecting members, (sometimes not required), atmosphere temperatures, pre-vibration shapes for each wires, and constraint conditions for each electric wires. To set those necessary items, an input screen (not shown) is presented on the display device 53, and necessary items are entered to the input screen by use of the input device 52.

The types of the electric wires are the types of the electric wires whose bending life spans are to be predicted.

For the electric wires, geometrical properties and material properties are linked to the types of the electric wires.

Specifically, the geometric properties include information about lengths and cross sections for each wire. The material properties are a moment of inertia of area, a polar moment of inertia of area, density a modulus of longitudinal elasticity, and a modulus of transverse elasticity. Those materials may be obtained in advance by tests, for example. Those properties concerns the finite elements in the stiffness matrix [K] of the expression (1). The atmosphere temperatures are temperatures around the electric wires and/or wire protecting members when the bending life span prediction is carried out, and typically −40° C., 0° C. and 25° C.

The pre-vibration shape is a shape of the electric wire or the like in a static state as indicated by reference numeral 1a in FIG. 7A. In the illustration, it is simplified and depicted linearly. The pre-vibration shape 1a may be manually entered by use of the input device 52, or a pre-vibration shape that was previously formed before the bending life span prediction may be used for the same. Preferably, such a pre-vibration shape as to satisfy given constraint conditions and the minimum bending radius of the electric wire is calculated in advance, and it is used for the pre-vibration shape 1a.

For the constraint conditions, information of perfect constraint, rotation constraint and perfect free are set, while corresponding to coordinate information on nodes n1 to n5 in FIG. 7A. The nodes n1 to n5 are connection points of the finite elements into which the electric wire is divided. Some of the nodes correspond in position to parts at which constraint members, such as connectors and clips, respectively. In this instance, the nodes n1 and n5 are put under the perfect or rotation constraint condition by the constraint members, while the remaining nodes n2 to n4 are put under the perfect free condition. The values set here concern the values of the finite elements in the displacement vector $\{x\}$ in the expression (1).

In some cases, the plural electric wires which form a wire harness are bundled, by an insulation locking band, tape or the like, into a single bundle, and in other cases, those electric wires are not bundled. In case where the electric wires are bundled together, the wire bundling is set as the constraint condition. In setting the constraint condition of the wire bundling, it is preferable to handle the electric wires that come in contact with the insulation locking band or tape in distinction from those located on the inner side of the former electric wires. By so doing, the bending life spans of the wires can be more exactly predicted since the electric wires bundled and the electric wires not bundled are separately processed.

In some cases, those electric wires are passed through a wire protecting member, such as a grommet, and in other cases, the electric wires are arranged or distributed without using the wire protecting member. The plural electric wires passed through the wire protecting member are used such that as described above, in some instances, those wires are bundled together into a single bundle, and in other instances, those wires are not bundled. In case where the wire protecting member is used, a constraint condition suitable for the wire protecting member is to be set. The step S1 thus far described corresponds to "setting step" and "setting unit" in claims.

Next, in a step S2, finite element models of the electric wires and/or wire protecting members are formed. The finite element model of the wire protecting member is formed by dividing the wire protecting member into plural rectangular finite elements. The finite element model of the electric wire is formed such that the electric wire is divided into plural beam elements. The step S2 corresponds to a finite element model forming step and a finite element model forming means in claims.

Next, in a step S3, a vibration analyzing process is carried out for each finite element. Specifically, in a step S301, on the assumption that a wire harness as a bundle of a plurality of electric wires as objects vibrates, the expression (4) applies to the wireharness to calculate a natural frequency of the wire harness. In this case, the geometric properties and the material properties as the individual elements of the stiffness matrix [K] are calculated on the assumption that those properties are the results of composing the geometric properties and the material properties of each electric wire and/or wire protecting member. For the natural frequency, its values corresponding to, for example, the first, second and tertiary vibration modes are calculated as shown in FIGS. 7A to 7C. The number of vibration modes to be calculated and the natural frequencies are not limited to the illustrated ones. For example, the first, second and tertiary vibration modes are set as default values, and may be changed by use of the input device 52.

Following the natural frequency calculation, steps S302 and S303 are executed in which the natural frequencies are applied to an expression obtained by Fourier transforming the expression (2) as described above to thereby calculate displacements and stresses of all the finite elements for each electric wire and/or wire protecting member. In this case, information as to whether or not the electric wires are bundled into one bundle and information as to whether or not specific electric wire or wires come in contact with the insulation locking band or the tape, which are set as the constraint conditions in the step S1, are incorporated regarding as the information concern all of the inertial matrix [M], the damping coefficient matrix [C], and the external force $\{F(t)\}$ in the expression (2).

In a step S304, the displacements and the stresses calculated every each natural frequency are linked with (finite elements) information of the position of each electric wire and/or wire protecting member as an object under prediction of the bending life, and a rewritten in to the result file. Those steps S3, S301 to S303 correspond to a vibration analyzing step and vibration analyzing unit in claims.

Subsequently, in a step S4, a maximum stress is retrieved from those stresses recorded in the result file, for each electric wire and/or wire protecting member under prediction of the bending life. In a step S5, a predicting function to the electric wire and/or wire protecting member under prediction of the bending life is read out. Specifically, a predicting function of the atmosphere temperature as set in the step S1 to the electric wire and/or wire protecting member under prediction of the bending life is read out from the bending life data file 55b stored in the storing device 55. The step S4 corresponds to a maximum stress retrieving step and a maximum stress retrieving unit in claims, and the step S5 corresponds to a predicting function readout step and predicting function readout unit in claims.

In the next step S6, each bending life span corresponding to maximum stress of each electric wire and/or each wire protecting member, which is obtained in the step S4, is acquired, while referring to the predicting functions read out in the step S5. From those bending life spans, a shortest bending life span is obtained. The shortest bending life span may be, for example, the number of bendings for endurance obtained from the bending life function in FIG. 4, or may be an endurance time calculated based on the number of bendings for endurance and the natural frequency corresponding to the former. The step S6 corresponds to a bending life predicting step and a bending life predicting unit in claims.

In the step S7, a position corresponding to the shortest bending life span is specified from its finite element. This position specifying is useful in locating a part of the wire at which the wire is possibly disconnected. In a step S8, the position specified in the step S7 and the bending life span predicted in the step S6 are output to the display device 53. Because the position on the wire protecting member and/or the electric wire corresponding to the shortest bending life span is output in addition to the bending life span, more accurate bending life prediction is ensured. The step S7 corresponds to a position specifying step and position specifying means in claims, and the step S8 corresponds an output step and an output unit in claims.

Figure 1:
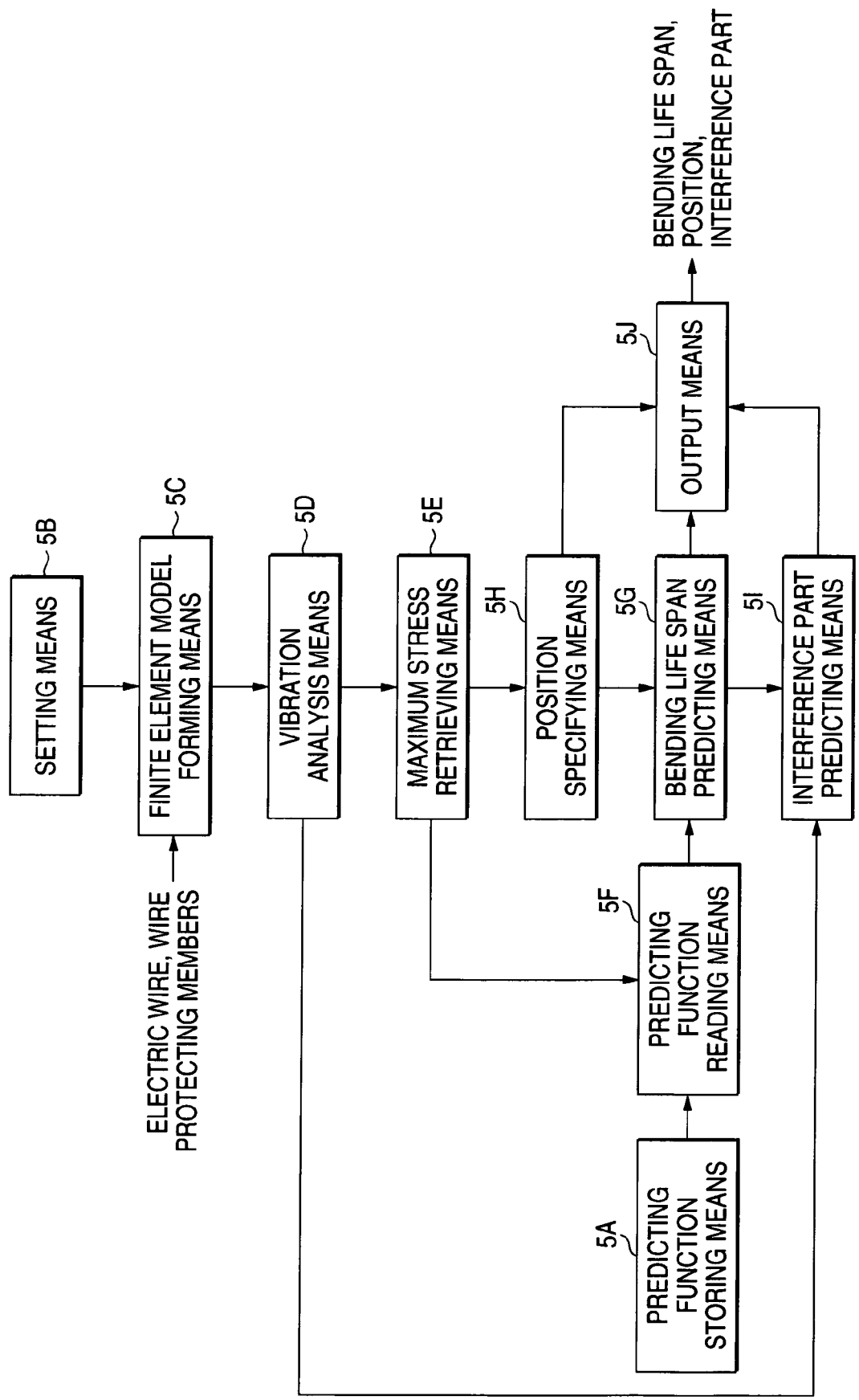
FIG. 1 is a block diagram showing a basic configuration of the present invention.

The following procedure may be taken: in a step S9, an interference part is predicted, and in a step S10 a predicted inference part is output. Specifically, as described in the step S304, the stresses calculated for each natural frequency are stored in the result file in a state that those stresses are linked with information of the positions (finite elements) of the electric wires and/or wire protecting members. Therefore, predictive shapes can be generated for each vibration mode from the result file, as indicated by 1a1 in FIG. 7A, 1a2 in FIG. 7B, and 1a3 in FIG. 7C. The position information of the obstacle 2, as described above, is stored in the storing device 55. Therefore, if the position information is composed with the predictive shape for each vibration mode, one can see that there is a possibility that the electric wire will interfere with the obstacle 2 (see FIG. 7C). On the contrary, it is possible to predict a part of the electric wire where it will interfere with the obstacle 2. The step S9 corresponds to an interference part predicting step in claims.

If in a step S11, it is judged that a command of outputting the result file is present, the contents of the result file 55c is output in the text format in a step S12. The output contents may be displayed by the display device 53 or printed on a sheet by the printing device 54. Further, the contents to be output may be designated by the input device 52. If the contents outputting is not needed, the sequence of processing steps may be ended (N in step S11). Thus, the embodiment of the invention succeeds in providing a method and apparatus for predicting bending life spans of electric wires or the like, which can more accurately predict bending life spans of the wires and can satisfactorily meet the demand of enhancing the prediction accuracy in an environment where vibrations occur, and a program for predicting the same in such ways. In particular, a disconnection life of the electric wire, which is due to engine vibration of the automobile, can be predicted for a short time and without performing the endurance test. This is a very advantageous effect. Further, also statistically, the bending life span is predicted under severe conditions. Accordingly, the embodiment contributes to further enhancement of quality and wiring path plan.

It will be readily understood that the invention is not limited to the embodiment above mentioned. For example, the wire protecting member is not limited to the grommet. Further, the invention is not limited to the inside of the automobile, but may be applied to a place in a factory where vibrations occur.

According to the invention, the plural electric wires, the atmosphere temperatures, pre-vibration shapes of the plural electric wires, and constraint conditions of the plural electric wires are set, and finite element models of plural electric wires are formed. Natural frequencies for the pre-vibration shapes of the plural electric wires are calculated, and stresses in individual finite elements of the finite element models which correspond to the natural frequencies are calculated, and a maximum stress is retrieved from the calculated stresses for each electric wire. Predicting functions corresponding to the plural electric wires and the atmosphere temperatures, which are set, are read out. A bending life span corresponding to the maximum stress of each electric wire, is acquired while referring to the predicting functions read out, and a shortest bending life span is obtained from the bending life spans, and output. Accordingly, the bending life spans of the plural electric wires can be accurately predicted without performing the endurance test. As a result, there is provided a bending life predicting method which can meet the demands of reducing the development period and enhancing the prediction accuracy.

According to the invention, the plural electric wires and wire protecting members, the atmosphere temperatures, pre-vibration shapes of the plural electric wires, and constraint conditions of the plural electric wires are set, and finite element models of plural electric wires are formed. Natural frequencies for the pre-vibration shapes of the plural electric wires are calculated, and stresses in individual finite elements of the finite element models which correspond to the natural frequencies are calculated, and a maximum stress is retrieved from the calculated stresses for each electric wire. Predicting functions corresponding to the plural electric wires and the atmosphere temperatures, which are set, are read out. A bending life span corresponding to the maximum stress of each electric wire, is acquired while referring to the predicting functions read out, and a shortest bending life span is obtained from the bending life spans, and output. Accordingly, the bending life spans of the plural electric wires inclusive of the wire protecting member can be accurately predicted without performing the endurance test. As a result, there is provided a bending life predicting method which can sufficiently meet the demands of reducing the development period.

According to the invention, the plural electric wires are regarded as a wire-like structure of a bundle of the plural electric wires, and natural frequencies of the plural electric wires are computed. This feature results in reduction of calculation amount. Further reduction of the time taken for the bending life span prediction is realized.

According to the invention, when the plural electric wires are bundled into a single bundle, and the bundling of the plural electric wires is set as one of the constraint conditions in the setting step. This ensures more exact prediction of the bending life span. Actually, in some cases, the plural electric wires are bundled into a single bundle, and in other cases, those are not bundled. The bending life span can be predicted, while those cases are clearly separated from each other.

According to the invention, a position specifying step for specifying a position on the wire protecting member or the electric wire corresponding to the shortest bending life span, is also specified, together with the bending life span, and is output. This feature ensures a more accurate prediction of the bending life span.

According to the invention, an interference part induced by vibrations on each wire protecting member or each plural electric wires is also predicted. Accordingly, with this feature, optimum wiring paths can be designed free from wire disconnection by its contact.

According to the invention, a curve representative of a lower confidence interval to a population regression function statistically calculated using data of the stresses and the number of bendings for endurance under a plurality of typical atmosphere temperatures for the wire protecting members and the electric wires, is used for the predicting function. Accordingly, the bending life span is predicted under severe statistical conditions. As a matter of course, a given statistical reliability on the predicting function is taken into account, and a computing process of the predicting function is easy. As a result, the bending life span is severely predicted without addition of complicated processing procedures. This contributes to further enhancement of quality and wiring path plan.

The invention claimed is:

1. A bending life predicting method of predicting a bending life span of each wire of a plurality of wires induced by vibration, at least two points of each of the plurality of wires being constrained, the method comprising the steps of:
   a pre-storing step of pre-storing each predicting function representing relationships among atmosphere temperatures, stresses and bending life spans for the plurality of wires;
   a setting step of setting the plurality of wires, the atmosphere temperatures, pre-vibration shapes of the plurality of wires, and constraint conditions of the plurality of wires;
   a finite element model forming step of forming finite element models of the plurality of wires by using a finite element method;
   a vibration analyzing step of calculating natural frequencies for the pre-vibration shapes and calculating stresses in individual finite elements of the finite element models which correspond to the natural frequencies, respectively;
   a maximum stress retrieving step of retrieving a maximum stress from the stresses calculated in the vibration analyzing step, for each of the plurality of wires;
   a predicting function readout step of reading predicting functions corresponding to the atmosphere temperatures set in the setting step, respectively;
   a bending life predicting step of acquiring a bending life span corresponding to the maximum stress of each of the plurality of wires while referring to the predicting functions read out in the predicting function readout step, and obtaining a shortest bending life span from the bending life spans; and
   an output step of outputting the shortest bending life span obtained in the bending life predicting step.

2. The method according to claim 1, wherein in the vibration analyzing step, the plurality of wires are regarded as a wiring structure in which the plurality of wires are bundled, and natural frequencies of each wire of the plurality of wires are computed, respectively.

3. The method according to claim 1, wherein the plurality of wires are bundled into a single bundle, and the bundling of the plurality of wires is set as one of the constraint conditions in the setting step.

4. Thu method according to claim 1, further comprising a position specifying step of specifying a position on the wire corresponding to the shortest bending life span, the output step outputting the position specified by the position specifying step.

5. The method according to claim 1, wherein
   in the vibration analyzing step, displacements of finite elements of the finite clement models which correspond to the natural frequencies are calculated,
   the method includes an interference part predicting step of predicting an interference part on the plurality of wires which is induced by vibrations bused on the calculated displacements, and
   the output step outputs the predicted interference part.

6. The method accord jag to claim 1, wherein a curve representing a lower confidence interval to a population regression function statistically calculated using the stresses and data on bending endurance life spans that are obtained under a plurality of typical atmosphere temperatures for the plurality of wires, is used for the predicting function.

7. A bending life predicting method of predicting a bending life span of each wire of a plurality of electric wires and wire protecting members for protecting the plurality of wires from bending, as induced by vibrations, at least two points of each of the plurality of wires being constrained, the method comprising:
   a pre-storing step of pre-storing relationships among atmosphere temperatures, stresses and bending life spans for plurality of wires and the wire protecting member;
   a setting step of setting the plurality of wires, the wire protecting member, the atmosphere temperatures, pre-vibration shapes of the plurality of wires and the wire protecting member, and constraint conditions of the plurality of wires and the wire protecting member;
   a finite clement model forming step of forming finite element models of the plurality of wires and the wire protecting member by using a finite element method;
   a vibration analyzing step of calculating natural frequencies for the pre-vibration shapes of each wire of the plurality of wire and the wire protecting member, and calculating stresses in individual finite elements of the finite element models which correspond to the natural frequencies, respectively;
   a maximum stress retrieving step of retrieving maximum stresses from the stresses calculated in the vibration analyzing step, for each of the plurality of wires and the wire protecting member;
   a predicting function readout step of reading predicting functions corresponding to atmosphere temperatures set in the setting step;
   a bending life predicting step of acquiring bending life spans corresponding to the maximum stresses of the plurality of wires and the wire protecting member, while referring to the predicting functions read out in the predicting function readout step, respectively, and obtaining a shortest bending life span from said bending life spans; and
   an output step of outputting the shortest bending life span obtained in the bending life predicting step.

8. The method according to claim 7, wherein in the vibration analyzing step, the plurality of wires are regarded as a wiring structure in which the plurality of wires are bundled, and the natural frequencies of each wire of the plurality of wires are computed, respectively.

9. The method according to claim 7, wherein the plurality of wires are bundled into a single bundle, and the bundling of the plurality of wires is set as one of the constraint conditions in the setting step.

10. The method according to claim 7, further comprising a position specifying step of specifying a position on the wire or the wire protecting member corresponding to the shortest bending life span, the output step outputting the position specified by the position specifying step.

11. The method according to claim 7, wherein
in the vibration analyzing step, displacements of finite elements of the finite element models which correspond to the natural frequencies are calculated,
the method includes an interference part predicting step of predicting an interference part on the plurality of wires which or the wire protecting member is induced by vibrations based on the calculated displacements, and
the output step outputs the predicted interference part.

12. The method according to claim 7, wherein a curve representing a lower confidence interval to a population regression function statistically calculated using the stresses and data on bending endurance life spans that are obtained under a plurality of atmosphere temperatures for the plurality of wires and the wire protecting member, is used for the predicting function.

13. A bending life predicting device for predicting bending life spans of each wire of a plurality of wires induced by vibrations, at least two points of each of the plurality of wires being constrained, the device comprising:
a computer connected to a storage device;
a pre-storing unit for pre-storing each predicting function representing relationships among atmosphere temperatures, stresses and bending life spans for the plurality of wires;
a setting unit of setting the plurality of wires, the atmosphere temperatures, pre-vibration shapes of the plurality of wires, and constraint conditions of the plurality of wires;
a finite element model forming unit for forming finite element models of the plurality of wires by using a finite element method;
a vibration analyzing unit for calculating natural frequencies for the pre-vibration shapes and calculating stresses in individual finite elements of the finite element models which correspond to the natural frequencies, respectively;
a maximum stress retrieving unit for retrieving a maximum stress from the stresses calculated in the vibration analyzing unit, for each of the plurality of wires;
a predicting function readout unit for reading predicting functions corresponding to the atmosphere temperatures set in the setting unit, respectively;
a bending life predicting unit for acquiring a bending life span corresponding to the maximum stress of each of the plurality of wires while referring to the predicting functions read out in the predicting function readout unit, and obtaining a shortest bending life span from the bending life spans; and
an output unit for outputting the shortest bending life span obtained in the bending life predicting unit.

14. The device according to claim 13, wherein
the vibration analyzing unit calculates displacements of finite elements of the finite element models which correspond to the natural frequencies,
the device includes an interference part predicting unit for predicting an interference part on the plurality of wires which or the wire protecting member is induced by vibrations based on the calculated displacements, and
the output unit outputs the predicted interference part.

15. A computer readable recording medium storing a program for predicting bending life spans of each wire of a plurality of wires induced by vibrations, at least two points of each of the plurality of wires being constrained, the program, when executed, causing a computer to function as:
a pre-storing unit for pre-storing each predicting function representing relationships among atmosphere temperatures, stresses and bending life spans for the plurality of wires;
a setting unit for setting the plurality for wires, the atmosphere temperatures, pre-vibration shapes of the plurality of wires, and constraint conditions of the plurality of wires;
a finite element model forming unit for forming finite element models of the plurality of wires by using a finite element method;
a vibration analyzing unit for calculating natural frequencies for the pre-vibration shapes and calculating stresses in individual finite elements of the finite clement models which correspond to the natural frequencies, respectively;
a maximum stress retrieving unit for retrieving a maximum stress from the stresses calculated in the vibration analyzing unit, for each of the plurality of wires;
a predicting function readout unit for reading predicting functions corresponding to the atmosphere temperatures set in the setting unit, respectively;
a bending life predicting unit for acquiring a bending life span corresponding to the maximum stress of each of the plurality of wires while referring to the predicting functions read out in the predicting function readout unit, and obtaining a shortest bending life span from the bonding life spans; and
an output unit for outputting the shortest bending life span obtained in the bending life predicting unit.

* * * * *